United States Patent [19]

Mish et al.

[11] Patent Number: 5,086,914
[45] Date of Patent: Feb. 11, 1992

[54] SUTURE PACKAGE

[75] Inventors: Stanley L. Mish; James D. Silverman, both of Flagstaff, Ariz.

[73] Assignee: W. L. Gore & Associates, Inc., Newark, Del.

[21] Appl. No.: 523,438

[22] Filed: May 14, 1990

[51] Int. Cl.⁵ .............................. A61B 17/06
[52] U.S. Cl. .................................... 206/63.3
[58] Field of Search ........................ 206/63.3

[56] References Cited

U.S. PATENT DOCUMENTS 3,280,971 10/1966 Regan, Jr. .
3,338,401 8/1967 Regan, Jr. .
3,490,192 1/1970 Regan, Jr. .
3,824,763 7/1974 Lewis .
4,693,365 9/1987 Corella ........................ 206/63.3

FOREIGN PATENT DOCUMENTS 1038713 9/1958 Fed. Rep. of Germany ..... 206/63.3
813683 3/1937 France ........................... 206/63.3
970876 6/1950 France ........................... 206/63.3

OTHER PUBLICATIONS

Les Bechdel and Slim Ray, River Rescue, 2nd ed. 1989, Appalachian Mountain Club Books, Boston, Massachusetts.

Primary Examiner—William I. Price
Attorney, Agent, or Firm—Wayne D. House

[57] ABSTRACT

A suture package comprising a housing surrounding a cavity and having a port through some portion of the housing, wherein said cavity contains a length of suture in a configuration sequentially ordered along the suture withdrawal path but otherwise random. In a preferred embodiment the cavity has a vent through a portion of the housing to allow the use of a gaseous flow to aid in the loading of the length of suture into the cavity. A method of suture packaging is also described.

22 Claims, 15 Drawing Sheets

FIGURE II

SUTURE PACKAGE

FIELD OF THE INVENTION

This invention relates to a suture package and a method of packaging sutures.

BACKGROUND OF THE INVENTION

Suture packages are designed to present sutures to the user in a clean, sterile and undamaged form, in a convenient and readily accessible manner, and in such a fashion that tangling or damage of the suture does not occur during removal from the package. The requirement to avoid tangling during removal has heretofore been accomplished by arranging the sutures in ordered and precise configurations within the package. This typically takes the form of placing a suture into a narrow, confining channel such as described in U.S. Pat. No. 3,338,401, or by arranging the suture into a precise configuration (generally with a winding technique) so that it cannot cross over itself during removal, as described in U.S. Pat. No. 4,496,045.

U.S. Pat. No. 3,338,401 also describes the use of a stream of air to carry the suture into the narrow, confining channel of the package. This package incorporates an entrance port for the suture and the carrying stream of air. A small vent is provided at the opposite end of the narrow confining channel to allow the stream of air to exhaust from the package.

While these previous packages function well in terms of product protection, sterility, convenience and avoidance of tangling, drawbacks exist in terms of the amount of space and materials required for these packages. In addition, these packages are often complex, relatively expensive and may require sophisticated equipment and/or excessive labor to perform the packaging operation.

It is readily apparent that the use of narrow, confining channels within the package or the use of precise, controlled configurations will require significant use of space and packaging materials. If multiple sutures are contained within the same package even more space and material is required. The space requirement can be seen to be a substantial problem when the quantity of sutures maintained in a typical large hospital inventory is taken into account. Likewise, these packages contribute significantly to hospital waste disposal problems.

The present invention allows the suture to be packaged and stored within a simple cavity in a configuration sequentially ordered along the suture withdrawal path but otherwise random. The cavity is dimensionally configured, that is of appropriate length, width and depth, to allow the suture to lie within the package in this sequentially ordered but otherwise random configuration. The cavity dimensions, particularly width, do not allow the suture to lie in an ordered or controlled configuration. After sequential loading of the suture into the cavity through the housing port, the suture package of the present invention allows a substantial length of suture material to be packaged within a small volume of space. Multiple sutures can be packaged within a small space by providing multiple cavities within a single package or, for single-armed sutures, by placing multiple sutures into a single cavity.

The smallest possible suture package configuration is that of a package containing a single suture. The package of the present invention having a single cavity containing a single suture can be made smaller than can be reliably held and opened by gloved human hands under operating room conditions. It is apparent that with the package of the present invention the size of a suture package has achieved the minimum practical limit.

The simplicity of the package of the present invention reduces the complexity of the packaging operation and the time required for that operation. The result can be a less expensive package that may require less space than previous packages, yet is at least equally as functional as previous packages.

It has been previously known to store ropes within cavities in a fashion similar to the suture package of the present invention. For example, ropes for whitewater rescue are stored within bags by inserting the first end of a rope into a bag and continuing to feed the length of rope into the bag until only the second end remains outside. The length of rope is thus stacked or piled within the bag in a configuration sequentially ordered along the withdrawal path but otherwise random. Ropes contained in such a fashion will pay out from the bag quickly and reliably without tangling.

For the purposes of this invention, a cavity is defined as a three dimensional space surrounded by a housing. The housing may have openings such as vents or ports. The phrase "in a configuration sequentially ordered along the suture withdrawal path but otherwise random" is herein meant to describe the arrangement of the suture within the package cavity wherein it is stored in the form of stacks or piles in a random configuration from which it is able to be withdrawn sequentially from the cavity via the port quickly and tangle-free in the fashion of rope withdrawn from the above described rope bag. The random configuration in which the suture lies within the cavity is the result of the suture having been fed sequentially through the port and into the cavity. As the suture is fed sequentially into the cavity, it piles or stacks into layer upon layer, with some overlap or crossover between layers. This imprecise stacking or layering is herein defined as a random configuration.

SUMMARY OF THE INVENTION

A suture package is described, the package comprising a housing surrounding a cavity and having a port through some part of the housing, wherein said cavity contains a suture arranged in a configuration sequentially ordered along the suture withdrawal path but otherwise random. The cavity is dimensionally configured to allow the suture to lie in this random configuration. The port allows the suture to be fed sequentially into the cavity, and also allows the suture to be sequentially withdrawn from the cavity. The sequentially ordered along the suture withdrawal path but otherwise random configuration in which the suture is stored within the cavity allows the suture to be withdrawn from the cavity when desired in a tangle-free manner. Preferably, the package also has a vent through a portion of the housing surrounding the cavity. In this embodiment a relatively high velocity gaseous stream is used to aid in quickly loading the suture into the cavity. The stream is directed into the cavity via the port simultaneously with one end of the suture and is thus used to carry the suture into the cavity in a sequential manner. The gaseous stream exhausts from the cavity through the vent. The vent is preferably so large as to be distributed about a substantial part of the cavity.

DETAILED DESCRIPTION OF THE INVENTION

Figure 1:
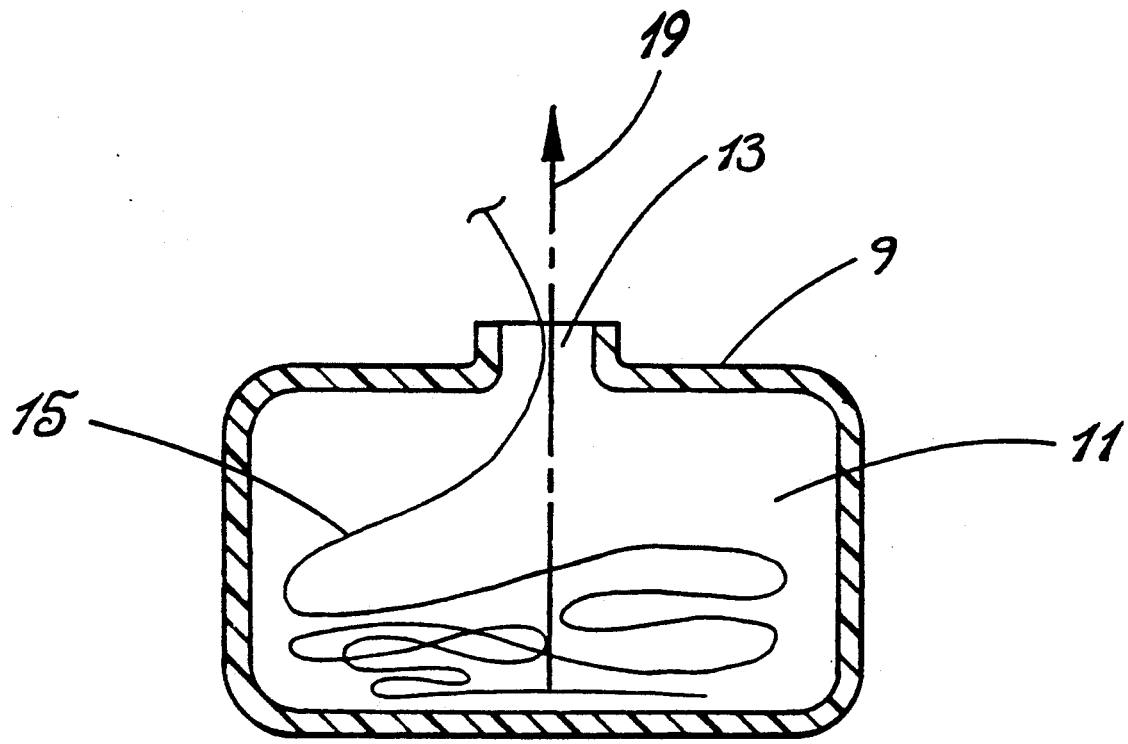
FIG. 1 shows the suture package of the present invention wherein a housing surrounds a cavity, said cavity has a port through some portion of the housing and said cavity contains a suture in a configuration sequentially ordered along the suture withdrawal path but otherwise random.

FIG. 1 shows the suture package of the present invention wherein a housing 9 surrounds a cavity 11, said cavity has a port 13 through some portion of the housing and said cavity contains a suture 15 in a configuration sequentially ordered along the suture withdrawal path but otherwise random. The suture was loaded into the cavity by inserting one end through the port and continuing to feed the suture sequentially through the port and into the cavity. The result of this process is that the suture lies within the cavity in a configuration sequentially ordered along the suture withdrawal path but otherwise random. As shown by the suture withdrawal path 19, the suture is easily and quickly withdrawn from the cavity via the port in a sequential and tangle-free manner. The cavity can be of any dimensions and shape that are adequate to allow the contained suture to pile or stack within the cavity in the form of a configuration sequentially ordered along the suture withdrawal path but otherwise random. The suture does not conform to any particular pattern such as would result from a cavity in the form of, for example, a narrow, confining channel. The cavity does not contain any channels, pins or other devices or forms that would result in the storing of the suture in an ordered configuration.

Figure 2:
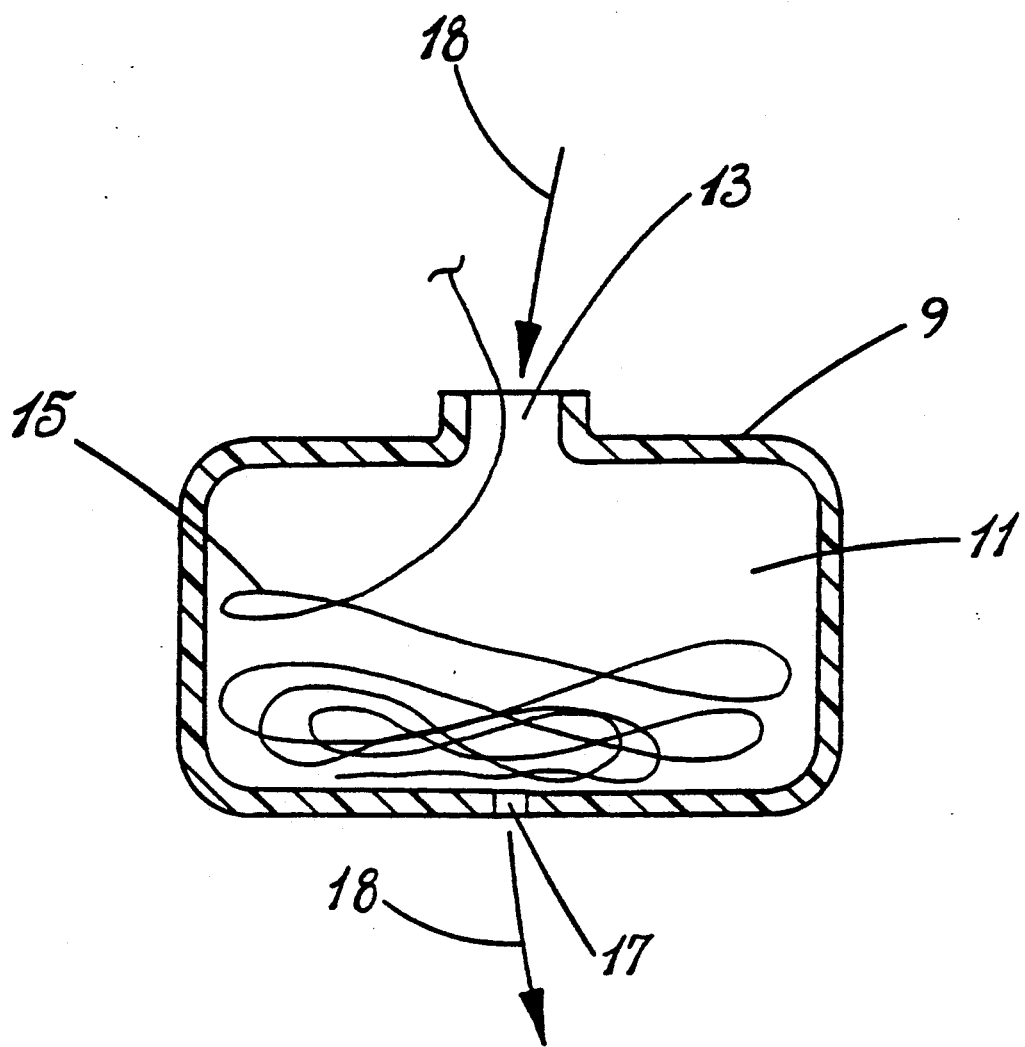
FIG. 2 shows a preferred embodiment of the present invention wherein a vent has been provided through some portion of the housing for the purpose of exhausting a gaseous stream from the cavity subsequent to the gaseous stream entering the port with the suture to aid in loading the suture into the cavity.

FIG. 2 shows a preferred embodiment of the present invention wherein a vent 17 has been provided through some portion of the housing 9 surrounding the cavity 11. The addition of the vent 17 allows the use of a gaseous stream, as indicated by the large arrows 18, to aid in the loading of a suture 15 into the package cavity 11. The gaseous stream is directed into the port 13 with one end of the suture to be loaded. The velocity of the gaseous stream then aids in carrying the suture into the package cavity in a sequential manner and allows it to pile or stack into the cavity in a random configuration. The gaseous stream exhausts from the cavity via the vent 17. The shape and location of the vent should be such that the suture is prevented from escaping from the cavity through the vent.

The gaseous stream is preferably in the form of a relatively high velocity flow of air. The flow may be provided from a compressed air source directed into the port 13 or from a vacuum applied to the vent 17. The use of a gaseous stream as a loading aid allows the suture to be loaded into the cavity very quickly. For example, times of less than one second have been required to load a single suture into a single cavity package of the present invention, using either a compressed air source or a vacuum source.

It is known to package some types of sutures, notably gut sutures, in liquid-filled packages. For sutures of this type, it would be feasible to use the liquid as an aid in loading the suture into the package of the present invention in the same manner as with the above described gaseous stream.

Figure 3:
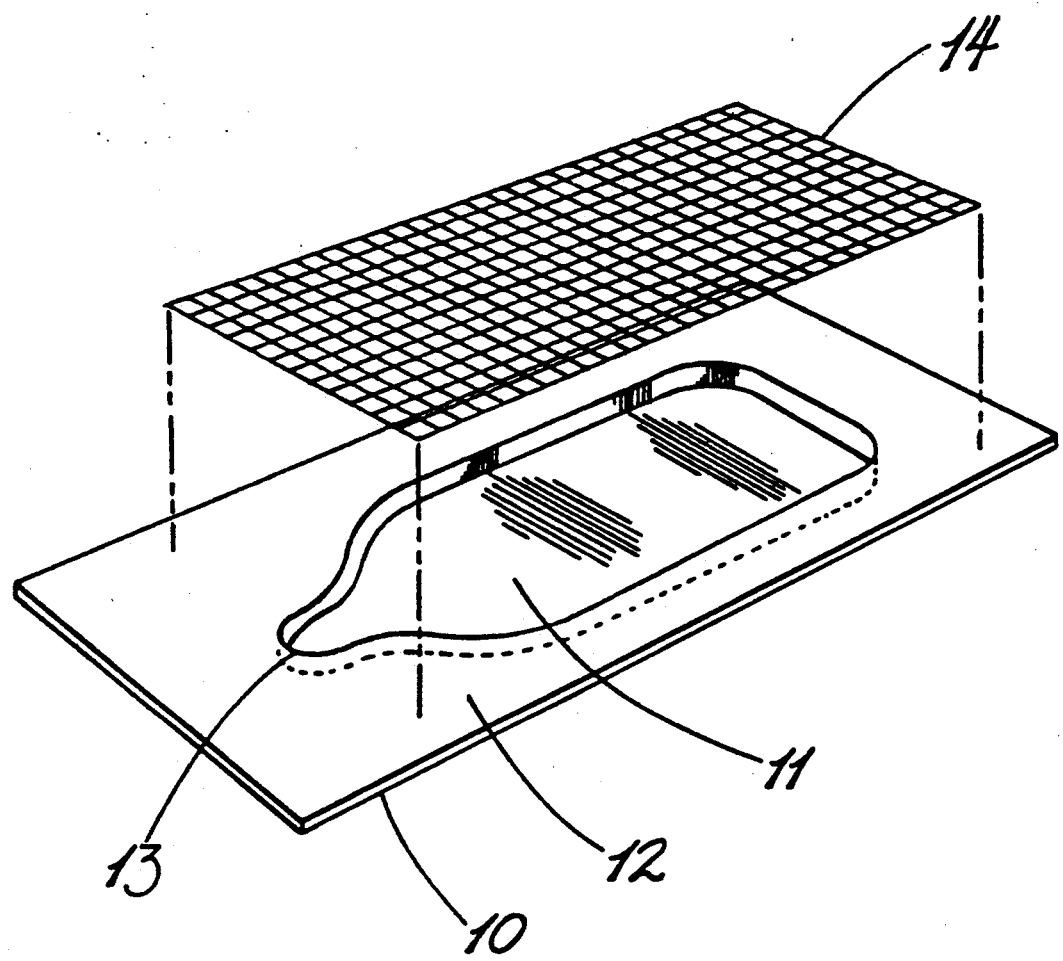
FIG. 3 shows a preferred embodiment of the present invention, comprising a cavity formed in a sheet of packaging material wherein the cavity has one open surface, a port connected to the cavity to allow entry of the suture, and a sheet of porous vent material intended to cover the open cavity surface.
Figure 4:
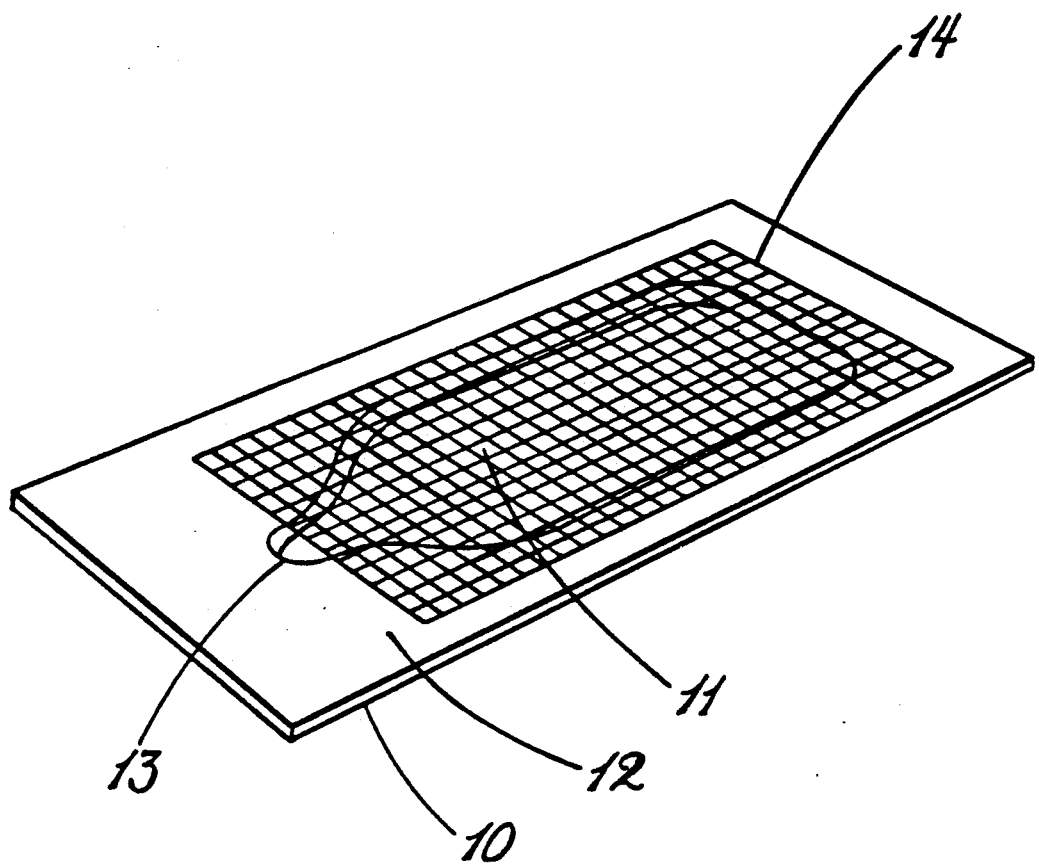
FIG. 4 shows a preferred embodiment after bonding the sheet of porous vent material to the flat surfaces of the sheet of packaging material adjacent to the cavity.

FIG. 3 shows a preferred embodiment of the present invention wherein a sheet of packaging material 10, preferably a plastic or a metal foil, has been formed to include a cavity 11. The cavity includes a port 13 through which the suture will be fed into the cavity 11. The open surface of the formed cavity 11 is closed with a sheet of porous vent material 14 for the preferred embodiment wherein the use of a large vented area produces a vent that is distributed about a substantial part of the cavity. The use of a sheet of porous vent material 14 provides a plurality of pore-shaped vents to allow the exhausting from the cavity of the gaseous stream used in loading the suture into the cavity. This porous vent material 14 is of length and width adequate to allow it to extend beyond the edges of the cavity 11 so that it may be bonded to the flat surface portion 12 of the sheet of packaging material 10 that is adjacent to the cavity 11. As shown by FIG. 4, the bonded sheet of porous vent material 14 does not cover the port 13.

The term bonded is herein meant to mean securely attached. Bonding may be accomplished with mechanical fastening means, with the use of a suitable adhesive or by the use of heat and/or pressure to cause the two surfaces to adhere.

Figure 5:
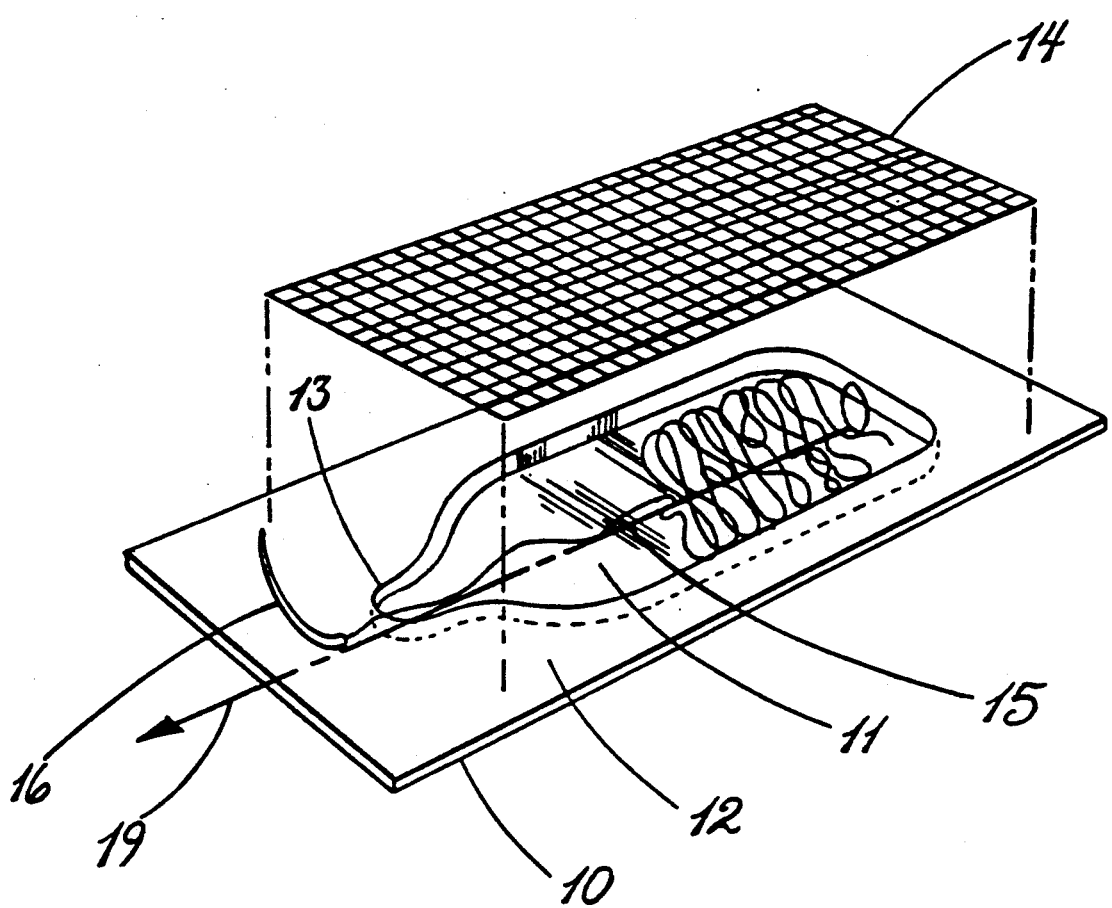
FIG. 5 shows a preferred embodiment package containing most of the length of a suture within the cavity in a configuration sequentially ordered along the suture withdrawal path but otherwise random.

FIG. 5 shows the preferred embodiment package containing a suture. This figure shows the sheet of porous vent material 14 not attached to the sheet of packaging material 10 for the sake of drawing clarity. In actuality the suture 15 is loaded into the package cavity 11 only after the sheet of porous vent material 14 has been bonded to the sheet of packaging material 10. The suture 15 lies within the cavity 11 in a configuration sequentially ordered along the suture withdrawal path but otherwise random. FIG. 5 also shows the armed end 16 of the suture remaining outside of the cavity 11. The needle and adjacent portion of suture may be held captive in any desired manner so long as the armed end of the suture is conveniently accessible so as to allow the easy grasping of the suture for sequential withdrawal from the cavity via the suture withdrawal path 19.

Figure 6:
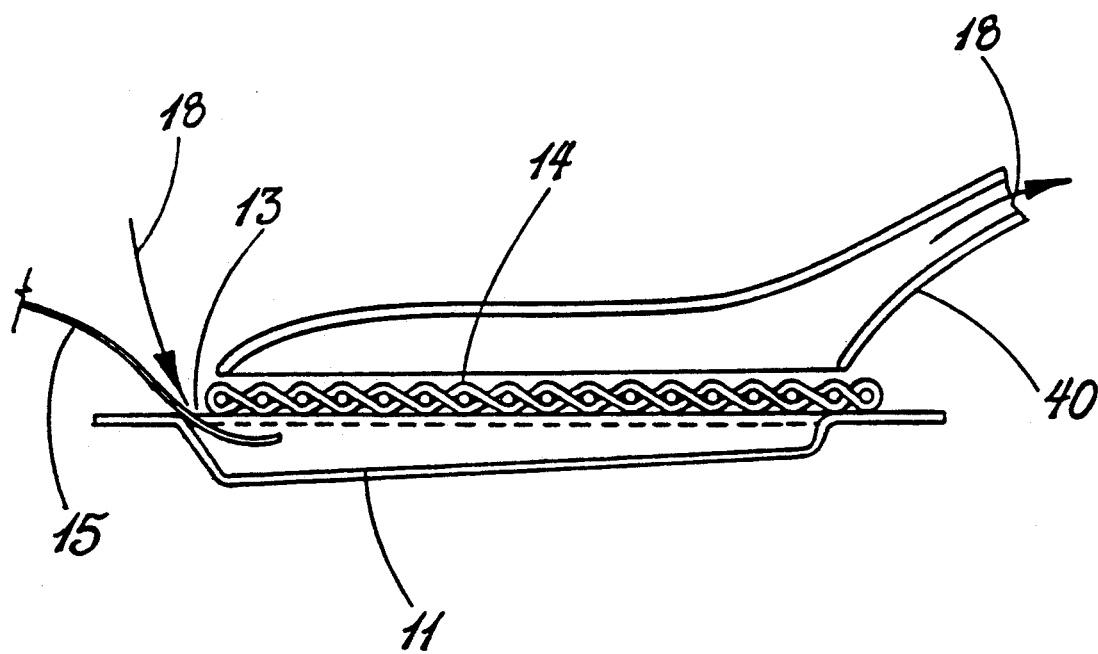
FIG. 6 shows a longitudinal section of a preferred embodiment wherein a suture is beginning to be loaded into the cavity with the aid of a vacuum source.
Figure 7:
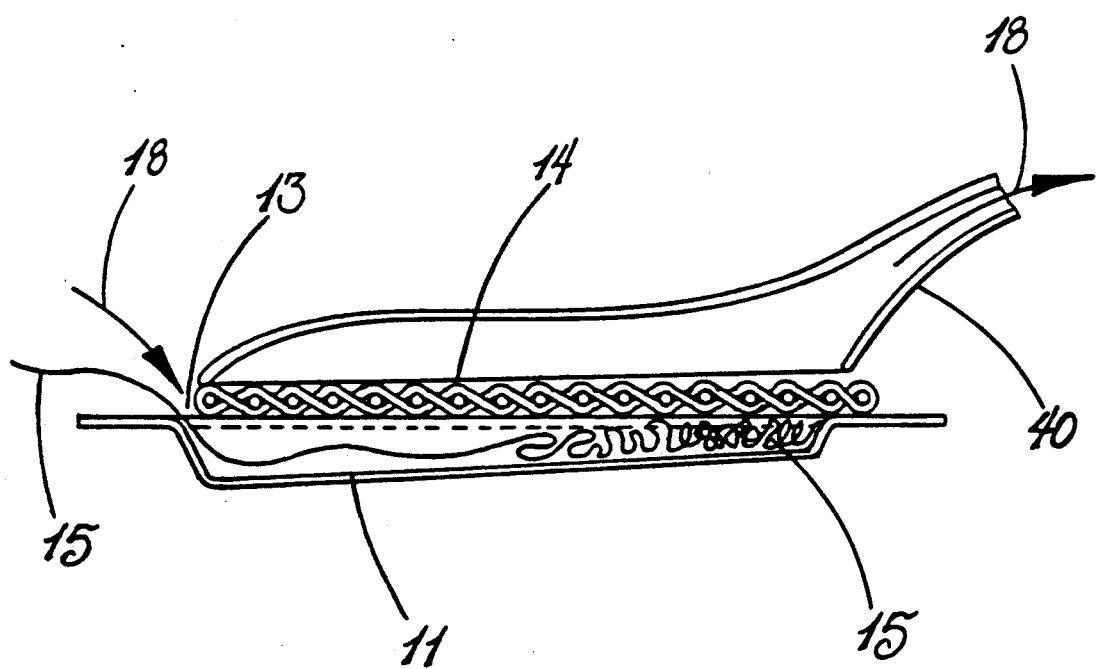
FIG. 7 shows a longitudinal section of a preferred embodiment wherein a suture has been loaded into the cavity with the aid of a vacuum source, the suture lying in a configuration sequentially ordered along the suture withdrawal path but otherwise random.

FIGS. 6 and 7 show longitudinal sections of a preferred embodiment of the inventive package with the suture being shown during the beginning phase of loading in FIG. 6 and just after the completion of loading the suture into the package in FIG. 7. For the preferred embodiment, loading is accomplished with the aid of a relatively high velocity flow of gas that enters the port 13 with the suture 15 and exhausts through the porous vent material 14, leaving the suture 15 packaged within the cavity 11 in a configuration sequentially ordered along the suture withdrawal path but otherwise random. FIGS. 6 and 7 show this accomplished with the use of a vacuum device 40 that pulls air and the suture 15 into the cavity 11 via the port 13 and then exhausts the air through the sheet of porous vent material 14. The flow of air in these figures is represented by the large arrows 18.

FIGS. 6 and 7 also show a cavity 11 having a greater depth at the end of the cavity adjacent to the port than at the opposite end. Such a tapered cavity can be useful in that it allows the use of a single cavity configuration to accommodate sutures of different diameters. Smaller diameter sutures are pulled by the gaseous stream to the shallower part of the tapered cavity and held securely while larger diameter sutures will pile up at a deeper portion of the cavity to also be held securely.

Figure 8:
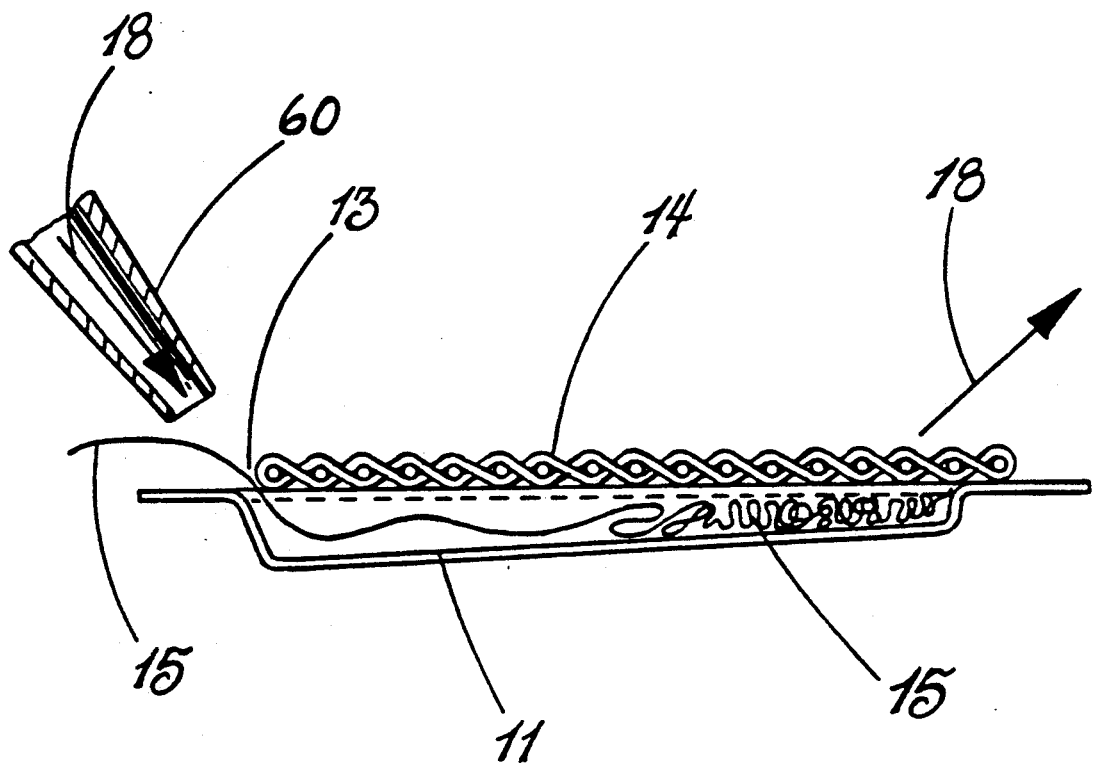
FIG. 8 shows a longitudinal section of a preferred embodiment wherein a suture has been loaded into the cavity with the aid of a positive pressure air source, the suture lying in a configuration sequentially ordered along the suture withdrawal path but otherwise random.

FIG. 8 shows another longitudinal section of a preferred embodiment package wherein the gaseous flow 18 is provided from a positive pressure source 60 such as compressed air that loads the suture 15 into the cavity 11 in the manner previously described.

Figure 9:
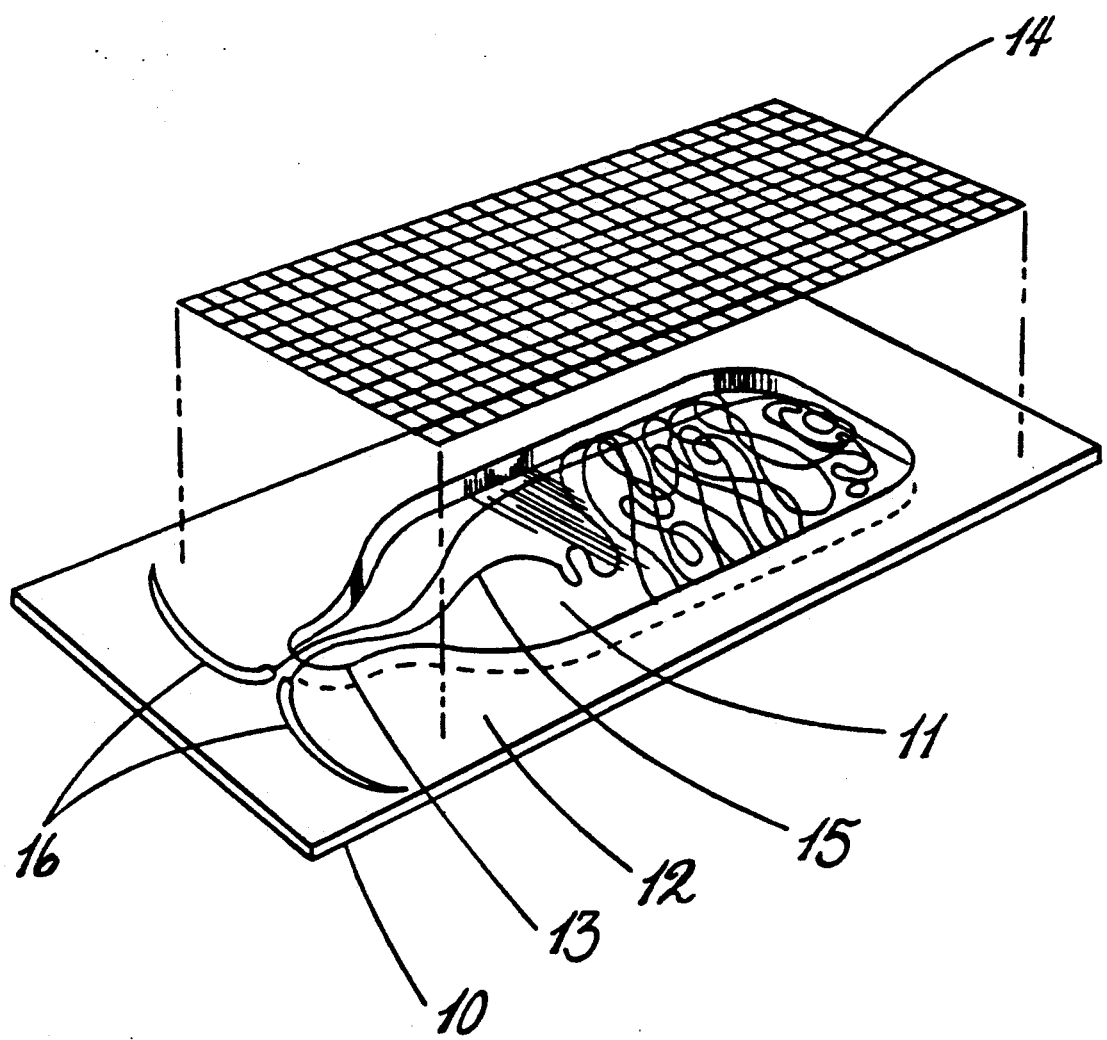
FIG. 9 shows a preferred embodiment package wherein most of the length of a double-armed suture has been loaded into the cavity in a configuration sequentially ordered along the suture withdrawal path but otherwise random.
Figure 10:
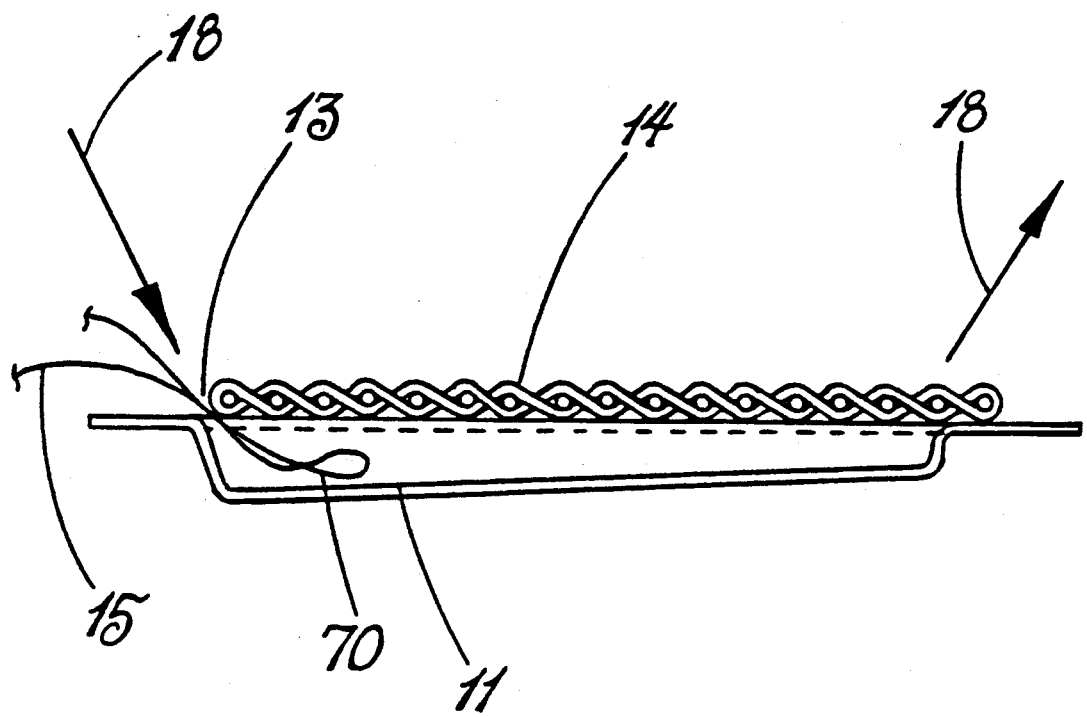
FIG. 10 shows a longitudinal section of a preferred embodiment wherein a double-armed suture is beginning to be loaded into the cavity with the aid of a vacuum source.

FIG. 9 depicts a preferred embodiment package wherein a double-armed suture, that is a suture having one needle attached to each suture end, has been loaded into the cavity 11. This is accomplished by folding the suture back on itself lengthwise so that the two segments are parallel and connected by a relatively sharp 180 bend in the suture. The suture is then loaded into the package as shown by FIG. 10 wherein the 180° bend 70 in the suture is inserted into the port 13. Gaseous stream is then used as described previously to load the suture into the cavity. The result is a double-armed suture loaded into the cavity in a configuration sequentially ordered along the suture withdrawal path but otherwise random as shown in FIG. 9.

If a gaseous stream of great enough velocity is used to load a suture having adequate flexibility, the suture can be loaded into the cavity simply by laying a very short portion of the length of suture over the port entrance 13 so that the high velocity gaseous stream pulls the suture into the port, folding the suture back on itself in the process as shown by FIG. 10.

Figure 11:
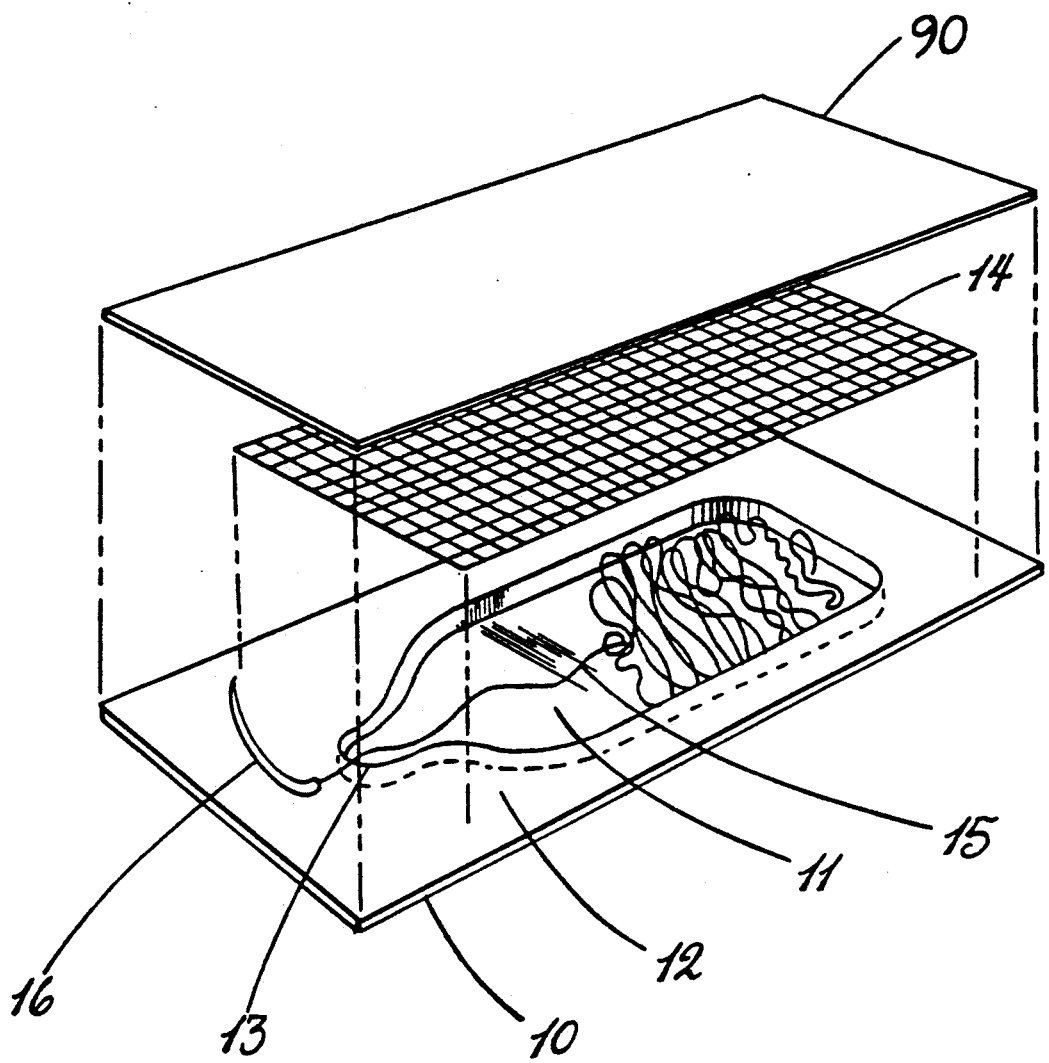
FIG. 11 shows a preferred embodiment of the present invention with the addition of a sheet of porous covering material bonded to the perimeter surfaces of the sheet of packaging material.

As shown by FIG. 11, after loading of the suture into the package cavity, an additional sheet of covering material 90 may be placed over and bonded to the flat surface 12 of the sheet of packaging material 10 in order to seal the suture into the package, serve as a bacterial barrier, and generally isolate it from the outside environment. This sheet of material may be non-porous or may be a porous material such as a suitable paper, or spun-bonded olefin fibers, for example Tyvek ® (E.I. duPont de Nemours), if it is necessary to subsequently access the suture with a sterilizing medium such as ethylene oxide or steam.

Figure 12:
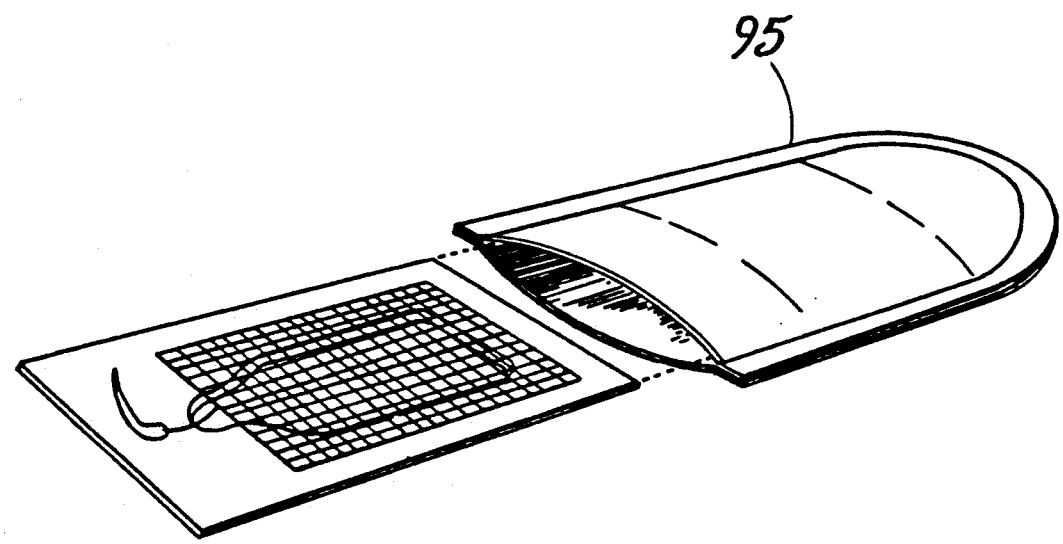
FIG. 12 shows an alternative embodiment wherein the suture cavity package is placed into and sealed within an additional envelope which is intended to serve as a bacterial barrier.

If desired, an additional envelope 95 may be placed around the package as shown in FIG. 12, closed and sealed to provide a double package around the suture wherein the additional envelope serves as a bacterial barrier. This is a common technique employed by medical device manufacturers to allow the inner package to be provided in sterile form in order to avoid contaminating a sterile operating field. The envelope material may also be of either porous or nonporous material so long as it serves as an effective bacterial barrier.

Figure 13:
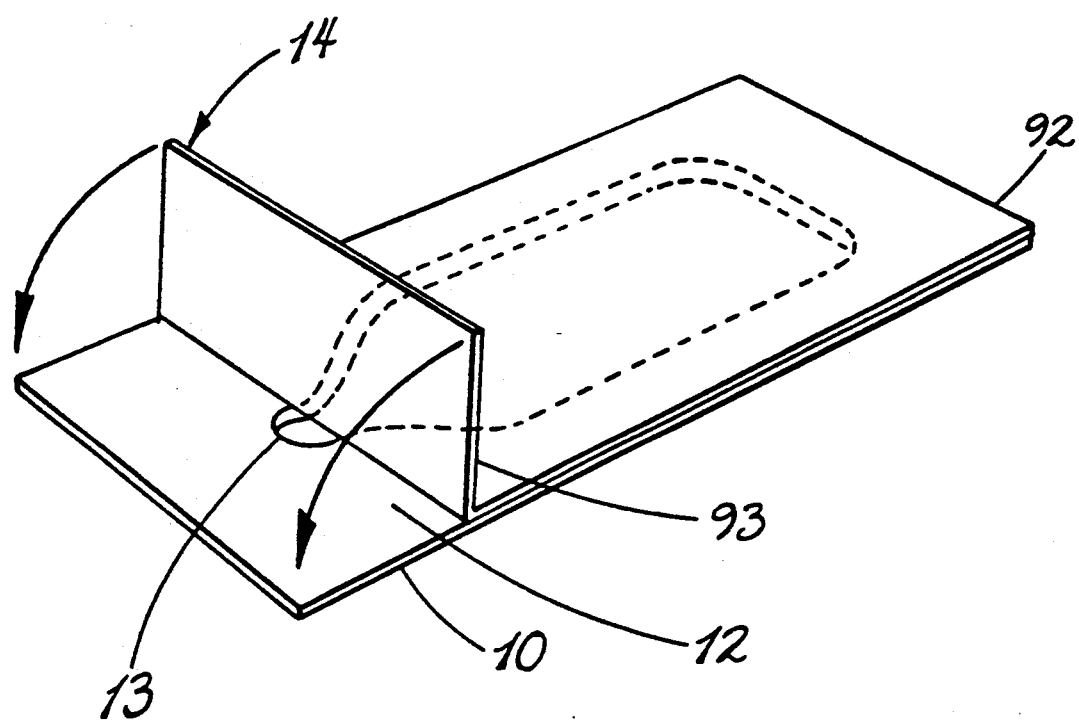
FIG. 13 shows an alternative embodiment wherein a sheet of porous covering material serves as both the cover material and the porous vent material.

FIG. 13 describes an embodiment wherein the sheet of porous vent material 14 forming the covering surface of the package cavity is the same sheet that serves as the cover for the package. In this case the cover sheet is a porous material such as spun-bonded olefin fibers that can allow the gaseous flow used to assist suture loading to escape the package. The covering sheet of porous vent material will subsequently serve as a protective bacterial barrier. As shown by FIG. 13, one end 92 of the covering sheet of porous vent material is permanently bonded to the flat surfaces 12 of the sheet of packaging material 10 adjacent to the cavity so as to cover the cavity while the other end 93 of the covering sheet of porous vent material is folded back to expose the port during loading of the suture. After loading, the edges of the folded back end of the covering sheet of porous vent material are then bonded to the edges of the sheet of packaging material. The bonding of the folded back end is preferably done in an impermanent, peelable fashion so that it may be peeled away from the sheet of packaging material during opening of the package to expose the suture needle and attached suture end. The needle may then be grasped to allow tangle-free withdrawal of the suture from the package cavity via the port.

Figure 14:
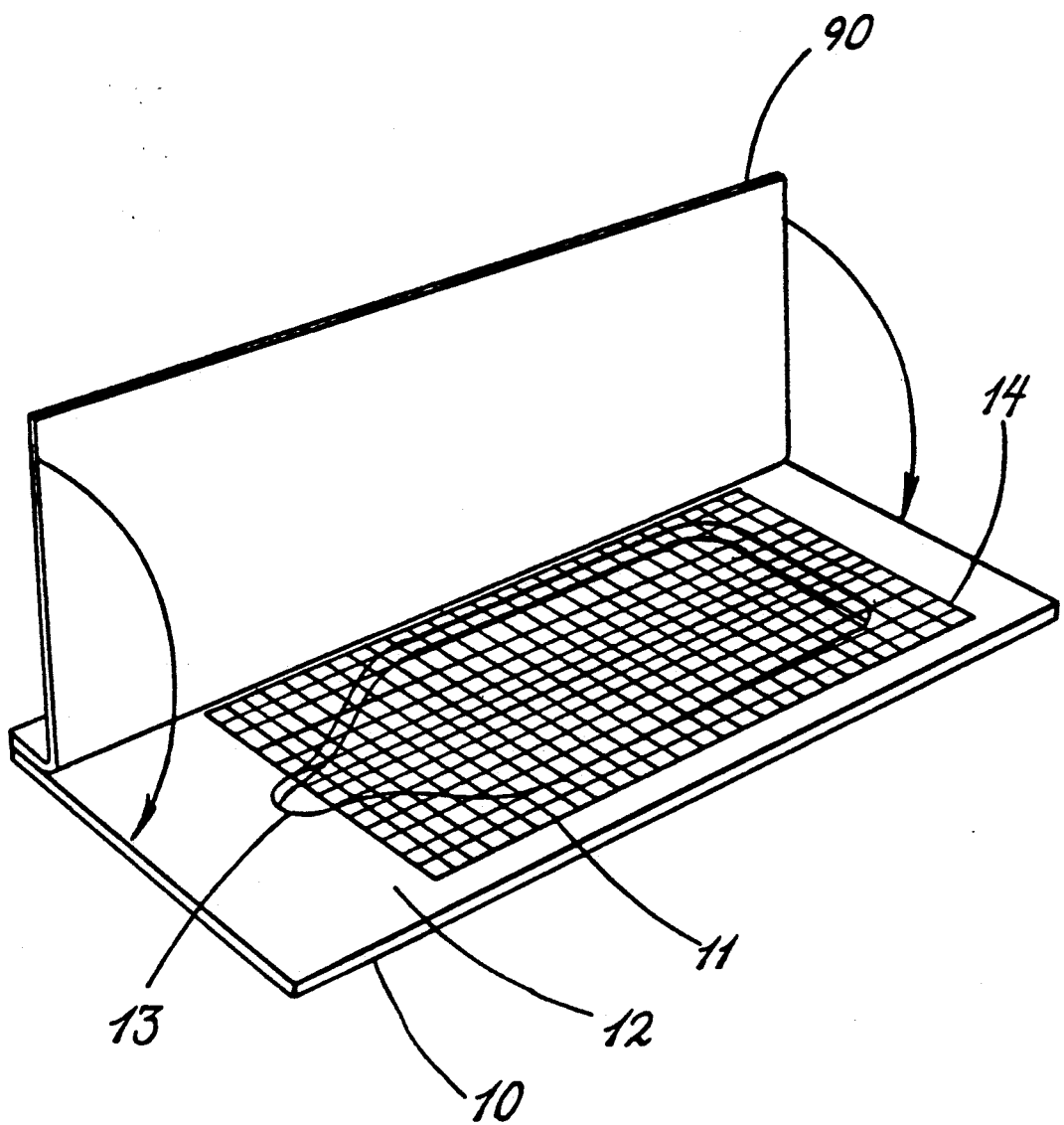
FIG. 14 shows an alternative embodiment wherein a sheet of porous covering material is bonded to only one edge of the sheet of packaging material in a hinged fashion which enables it to be bonded to the sheet of packaging material along its other edges after the suture has been loaded into the package.

FIG. 14 shows an embodiment wherein the sheet of covering material 90 is bonded to one edge of the sheet of packaging material in a hinged manner. This configuration allows easy packaging in that after the suture is loaded into the package cavity, the sheet of covering material 90 is folded down to contact the other edges of the sheet of packaging material and bonded to these edges.

Figure 15:
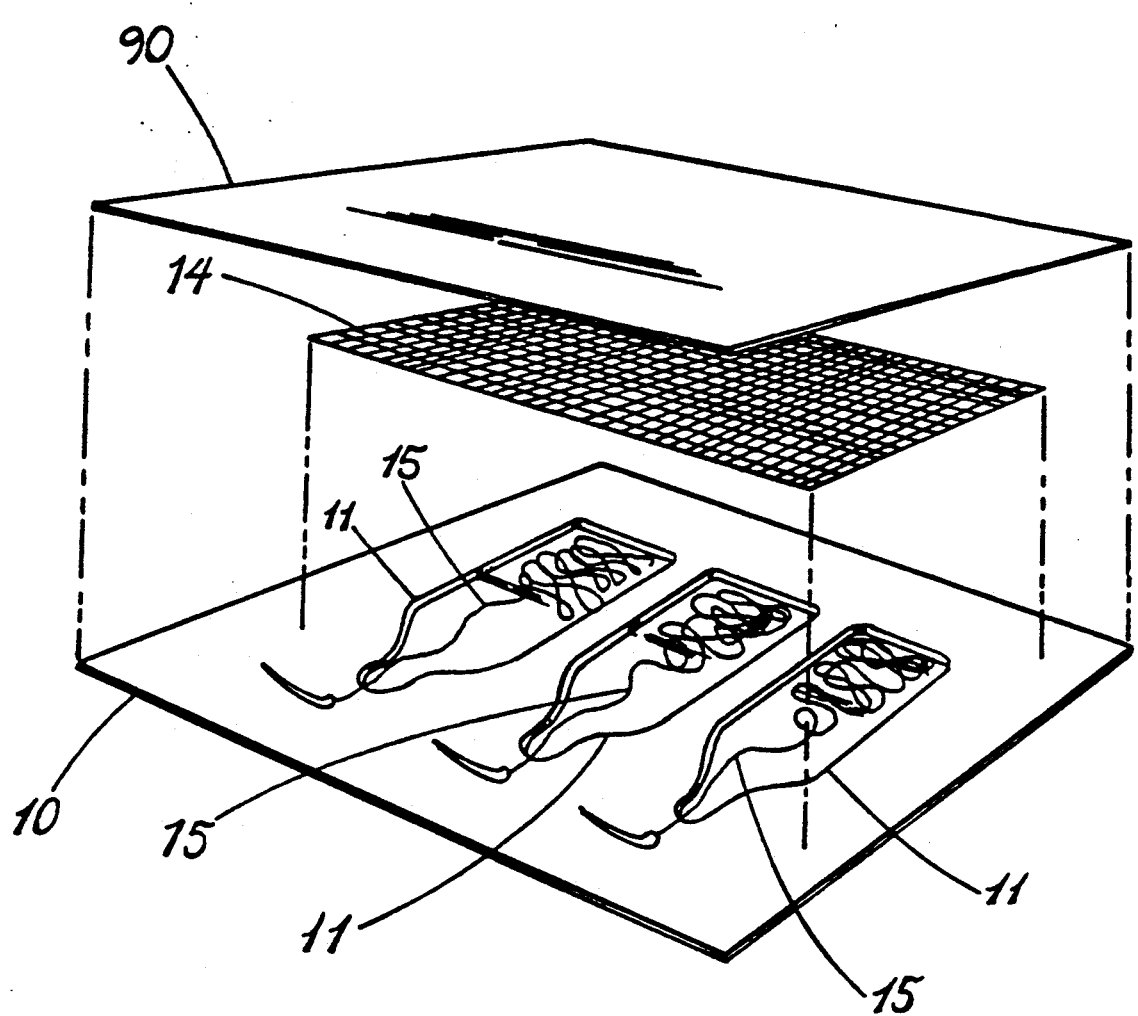
FIG. 15 shows an alternative embodiment wherein the sheet of packaging material contains multiple cavities for the packaging of multiple sutures, wherein each suture is contained in a configuration sequentially ordered along the suture withdrawal path but otherwise random.

As shown by FIG. 15, the package of the present invention can be made to have more than one cavity 11 within a single package to allow the packaging of multiple sutures within a single package. This concept further reduces the volume of packaging material relative to the number of sutures provided. Furthermore, it is possible to package more than one single-armed suture within a single cavity if the individual sutures are loaded one after another, that is if the loading of the second suture is not begun until the completion of the loading of the first suture. When multiple sutures are loaded into a cavity in this manner, it does not matter which suture is withdrawn from the package first. The loading of more than one double-armed suture into a single cavity is also possible as long as each suture is removed in sequence opposite to that in which the sutures are loaded.

One method of loading more than one suture into a single cavity is to insert one end of each suture into the port and apply a gaseous stream while restraining all sutures but one so that only the one suture is carried into the cavity. The next suture to be loaded is then released from its restraint allowing it to be carried into the cavity. In this fashion all sutures are loaded into the same cavity one after another.

The selection of materials including any bonding agents that are suitable for the inventive suture packages may be readily accomplished by those skilled in the art of medical device packaging. Selection criteria include cleanliness, toxicity, smoothness, mechanical strength and shape retention, porosity and bacteria impermeability, temperature capability, compatibility with the desired sterilization technique, expense and recyclability. Packaging materials may include formable or moldable plastics such as polyvinyl chloride, polypropylene, polyethylene terephthalate, polyethylene, fluoropolymers, polyphthalate carbonate, metal foils, etc. Porous vent materials may include various plastic or metal screens and materials such as spunbonded olefin fibers or expanded polytetrafluoroethylene.

Cavities of relatively greater width may be required for relatively stiff sutures as the number of bends may be reduced and the radius of those bends may be increased. Relatively greater velocity gaseous flows may also be necessary to aid in packaging relatively stiff sutures. It appears that sutures of any commonly used suture material may be packaged in the package of the present invention. The most easily loaded sutures appear to be those of porous polytetrafluoroethylene because of their flexibility and lubricious surfaces.

We claim:

1. A suture package comprising:
    a housing defining at least one enclosed cavity;
    a port in said housing configured to permit lengthwise insertion of suture material into said cavity; and
    venting means in said housing distributed about a substantial part of said cavity for venting gas from said cavity and being operative during the insertion of suture material through said port.

2. The suture package as in claim 1 wherein said cavity and said port together define a suture withdrawal path, and wherein said venting means is distributed along said withdrawal path.

3. The suture package as in claim 1 wherein said venting means includes a plurality of pore-shaped vents.

4. The suture package as in claim 1 wherein said housing comprises at least one sheet member forming a planar wall and having a recess defining at least part of said cavity, and wherein said housing includes a second sheet member juxtaposed against said first sheet member to only partially cover said recess, the part of said recess uncovered defining said port.

5. The suture package as in claim 4 wherein said recess includes an elongated portion having a tip end, and wherein said tip end is the recess part not covered.

6. The suture package as in claim 4 wherein said recess has width and thickness dimensions, and wherein said recess is tapered to narrow in at least one of said width and thickness dimensions in a direction away from said port.

7. The suture package as in claim 4 wherein said venting means includes said second sheet member being formed of a porous material.

8. The suture package as in claim 7 wherein said port also is configured to permit lengthwise withdrawal of suture material from said cavity during use, wherein said second sheet includes a folded edge, said second sheet being foldable at said edge to cover said port after suture insertion and unfoldable to uncover said port to allow suture withdrawal.

9. The suture package as in claim 7 further including a third sheet member hingedly attached to said housing to cover both said second sheet member and said port following insertion of a suture, for providing a bacterial barrier.

10. The suture package as in claim 1 wherein at least a part of said housing is formed from a substantially gas-impermeable material, and wherein said vent means includes another part of said housing being formed of a porous material, the dimensions of the pores of said material being selected to allow venting of gas while blocking escape of suture material from said cavity.

11. The suture package as in claim 11 wherein said cavity is elongated and has opposing ends and said port is positioned at one opposing end, and wherein said porous material housing part extends along substantially the entire elongated cavity.

12. The suture package as in claim 10 wherein said porous material also is a bacterial barrier.

13. The suture package as in claim 1 further including at least one length of suture material disposed in said cavity.

14. The suture package as in claim 13 wherein said port and said cavity together define a suture withdrawal path, and wherein said at least one length is disposed in said cavity in a configuration sequentially ordered along the suture withdrawal path but otherwise random.

15. The suture package as in claim 14 wherein at least two lengths of suture material are sequentially disposed along said suture withdrawal path in said cavity with respect to one another, the suture material of each of said two lengths being disposed in a configuration sequentially ordered along said withdrawal path but otherwise random.

16. The suture package of claim 13 further including a sealed protective envelope surrounding said housing and said disposed suture material.

17. The suture package as in claim 14 wherein said one length is doubled back on itself to form a double-armed suture, and wherein at least one arm of said double-armed suture is disposed in a configuration sequentially ordered along said withdrawal path but otherwise random.

18. A filled suture package comprising a housing defining at least one cavity, a length of suture material disposed in said cavity, and a port in said housing for withdrawing said suture material and, together with said cavity, defining a suture withdrawal path, said suture material being disposed in a configuration sequentially ordered along said withdrawal path but otherwise random, wherein at least a portion of said housing is substantially permeable to sterilizing gases but substantially impermeable to bacteria.

19. The filled suture package as in claim 18 wherein said housing portion includes at least an inner layer and an outer layer, said inner layer being more porous than said outer layer.

20. The filled suture package as in claim 18 further including a sealed envelope surrounding said housing, said envelope being impermeable to bacteria.

21. The filled suture package as in claim 18 including at least two lengths of said disposed suture material in said cavity, one of said two lengths being disposed sequentially behind the other relative to said port along said withdrawal path.

22. The filled suture package as in claim 18 wherein said housing defines a plurality of separate cavities and includes a separate port associated with each of said cavities, each of said cavities including at least one length of suture material disposed therein in a configuration sequentially ordered along a withdrawal path extending from the cavity through said respective port but otherwise random.

* * * * *